(12) United States Patent
Park

(10) Patent No.: US 7,784,357 B2
(45) Date of Patent: Aug. 31, 2010

(54) CREEP TESTER FOR PRECISION LOAD CONTROL WITH WEIGHT

(75) Inventor: Dong Su Park, Daejeon (KR)

(73) Assignee: Korea Electric Power Corporation, Seoul (KR)

( * ) Notice: Subject to any disclaimer, the term of this patent is extended or adjusted under 35 U.S.C. 154(b) by 64 days.

(21) Appl. No.: 11/942,517

(22) Filed: Nov. 19, 2007

(65) Prior Publication Data

US 2009/0007691 A1    Jan. 8, 2009

(30) Foreign Application Priority Data

Jul. 3, 2007    (KR)    ...................... 10-2007-0066411

(51) Int. Cl.
*G01N 3/02* (2006.01)
*G01N 3/08* (2006.01)
*G01N 11/00* (2006.01)

(52) U.S. Cl. .............................. 73/859; 73/803; 73/824; 73/823

(58) Field of Classification Search .................... 73/781, 73/782, 790, 803, 813, 818, 823–824, 859
See application file for complete search history.

(56) References Cited

U.S. PATENT DOCUMENTS

| | | | | |
|---|---|---|---|---|
| 575,651 A | * | 1/1897 | Kidwell | 73/770 |
| 642,978 A | * | 2/1900 | Hasse | 73/803 |
| 1,630,110 A | * | 5/1927 | Cole | 73/818 |
| 1,811,210 A | * | 6/1931 | Olsen | 73/803 |
| 2,278,416 A | * | 4/1942 | Atti | 73/818 |
| 2,291,106 A | * | 7/1942 | Ruch | 73/825 |
| 2,331,577 A | * | 10/1943 | Sonntag | 73/816 |
| 2,344,133 A | * | 3/1944 | Davis, Jr. | 60/328 |
| 2,376,814 A | * | 5/1945 | Robinson | 73/818 |
| 2,703,492 A | * | 3/1955 | Brissette et al. | 73/818 |

(Continued)

FOREIGN PATENT DOCUMENTS

JP    58166241 A    * 10/1983

OTHER PUBLICATIONS

Morrison et al. "Design-Development of a Variable Load Tension-Compression Creep Testing Machine" The Journal of Strain Analysis for Engineering Design. vol. 21, No. 1, 1986 pp. 25-31.*

(Continued)

*Primary Examiner*—Lisa M Caputo
*Assistant Examiner*—Jonathan Dunlap
(74) *Attorney, Agent, or Firm*—Kenyon & Kenyon LLP

(57) ABSTRACT

A creep tester for a precise and accurate creep test includes a movable actuator capable of loading corresponding to change in length of a specimen, a cam actuator operated in association with the movable actuator, and a self weight actuator. The movable actuator includes upper and lower spherical adjusting seats to hold upper and lower portions of the specimen, a spring disposed on the upper spherical adjusting seat to correspond to a minute deformation of the specimen, upper and lower movable tables respectively contacting the spring and the lower spherical adjusting seat, a load cell and a stationary table disposed on the upper movable table, and a movable loading table disposed below the lower movable table to apply a predetermined load to the specimen. The creep tester can perform a precise creep test by continuously applying a constant load without supplementation of hydraulic pressure.

4 Claims, 5 Drawing Sheets

U.S. PATENT DOCUMENTS

| | | | | |
|---|---|---|---|---|
| 2,933,921 | A * | 4/1960 | Gloor | 73/795 |
| 3,120,753 | A * | 2/1964 | Green et al. | 73/81 |
| 3,127,765 | A * | 4/1964 | O'Neil | 73/795 |
| 3,394,384 | A * | 7/1968 | Hines | 346/32 |
| 3,464,260 | A * | 9/1969 | Heyman | 73/806 |
| 3,470,737 | A * | 10/1969 | Fridley | 73/81 |
| 3,665,757 | A * | 5/1972 | Hoag | 73/818 |
| 3,786,676 | A * | 1/1974 | Korolyshun et al. | 73/817 |
| 3,854,328 | A * | 12/1974 | Schmidt | 73/813 |
| 4,004,457 | A * | 1/1977 | Eide et al. | 73/818 |
| 4,182,192 | A * | 1/1980 | Argabrite et al. | 73/818 |
| 4,478,086 | A * | 10/1984 | Gram | 73/781 |
| 4,658,921 | A * | 4/1987 | Karpa | 177/50 |
| 4,812,052 | A * | 3/1989 | Adam et al. | 374/50 |
| 4,825,700 | A * | 5/1989 | Vardoulakis et al. | 73/749 |
| 4,885,941 | A * | 12/1989 | Vardoulakis et al. | 73/794 |
| 4,972,719 | A * | 11/1990 | Vinson et al. | 73/790 |
| 5,090,249 | A * | 2/1992 | Bielewicz | 73/822 |
| 5,361,640 | A * | 11/1994 | Carroll et al. | 73/831 |
| 5,373,744 | A * | 12/1994 | Parsons et al. | 73/818 |
| 5,693,890 | A * | 12/1997 | Holmes | 73/856 |
| 5,959,215 | A * | 9/1999 | Ono et al. | 73/798 |
| 5,987,961 | A * | 11/1999 | Harris et al. | 73/11.01 |
| 6,813,961 | B2 * | 11/2004 | Stiller et al. | 73/818 |
| 7,404,334 | B2 * | 7/2008 | Saari et al. | 73/856 |
| 7,441,468 | B2 * | 10/2008 | Cox | 73/820 |
| 7,513,168 | B2 * | 4/2009 | Alba | 73/826 |
| 2002/0069705 | A1 * | 6/2002 | Stiller et al. | 73/788 |
| 2005/0050963 | A1 * | 3/2005 | Shelby | 73/809 |

OTHER PUBLICATIONS

F.N. Cogswell. "Tensile Deformations in Molten Polymers" Rheologica Acta, Originals, Chemistry and Materials Science. vol. 8, No. 2, Jul. 1969 pp. 187-194.*

Kevin Smith. "Compression Creep of a Pultruded E-glass/polyester Composite at Elevated Service Temperatures" Thesis: Georgia Institute of Technology, Jul. 18, 2005 <http://smartech.gatech.edu/bitstream/1853/7195/1/smith_kevin_j_200508_mast.pdf>.*

V.R. Parameswaran. "Cyclic Creep of Frozen Soils" Proceedings of the Fourth International Symposium on Ground Freezing. vol. 2, Aug. 5, 1985 pp. 201-206.*

* cited by examiner

_US 7,784,357 B2_

CREEP TESTER FOR PRECISION LOAD CONTROL WITH WEIGHT

CROSS-REFERENCE TO RELATED APPLICATIONS

The present application claims priority to Application No. 10-2007-0066411, filed in the Republic of Korea on Jul. 3, 2007, which is expressly incorporated herein in its entirety by reference thereto.

FIELD OF THE INVENTION

The present invention relates to a creep tester for a precise and accurate creep test in structural testing of concrete and other construction materials, and more particularly to a creep tester for precision load control with self weight, which can perform a precise creep test by continuously applying a semi-permanently constant load without supplementation of hydraulic pressure by external electrical means or manual operations.

BACKGROUND INFORMATION

Storage buildings of nuclear power plants are generally constructed by a post-tensioning construction method to obtain structural reinforcement. In the post-tensioning construction method, a load is applied based on a design value of an initial tensioning amount, which is obtained by calculating a creep amount related to a concrete tensioning amount and other reasons. Therefore, since the creep amount of concrete must be obtained by an actual experiment before post-tensioning construction of the storage buildings, it is necessary to measure a precise creep amount.

A conventional creep tester for measuring the creep amount is generally designed to apply a load of about 50 tons with a hydraulic jack.

Therefore, it is necessary for the conventional creep tester to have an apparatus for applying hydraulic pressure, that is, a hydraulic pressure actuator. However, since it is impossible to achieve complete sealing due to characteristics of hydraulic pressure, the hydraulic pressure actuator requires periodic supplementation of hydraulic pressure to have a constant hydraulic pressure during operation.

As such, since the conventional creep tester using the hydraulic pressure experiences a decrease in hydraulic pressure with elapse of time, a manual operation or a separate electrical device must be performed or used for continuous supplementation of the hydraulic pressure. However, since such a manual operation or a separate electrical device is also operated based on detection of sensors in a predetermined range of hydraulic pressure, they have a problem in that a precise load cannot be continuously applied to test concrete samples.

SUMMARY

Example embodiments of the present invention address such problems of the conventional techniques as described above, and example embodiments of the present invention provide a creep tester for precise load control with self weight that can keep a constant hydraulic pressure even with elapse of time to perform an accurate and precise creep test.

According to example embodiments of the present invention, a creep tester for measuring creep characteristics of construction material includes a movable actuator capable of loading corresponding to change in length of a concrete specimen prepared as construction material for testing, a cam actuator operated in association with the movable actuator, and a self weight actuator to actuate the cam actuator. The creep tester is operated using a predetermined weight based on a principle of leverage.

Further features and aspects of example embodiments of the present invention are described in more detail below with reference to the appended Figures.

DETAILED DESCRIPTION

Figure 1:
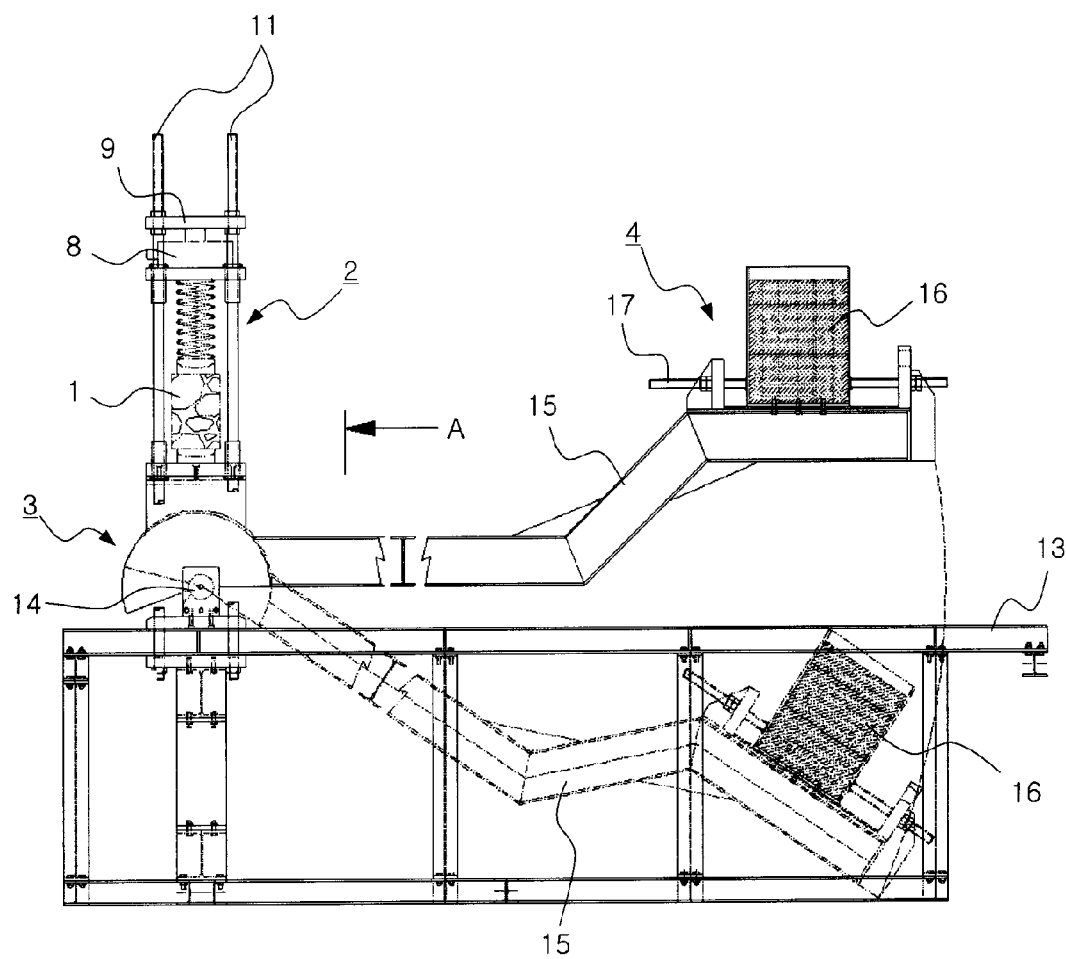
FIG. 1 is a front view of a creep tester for precise load control with a self load according to an exemplary embodiment of the present invention.

Exemplary embodiments of the present invention are described in detail with reference to the appended Figures. Like reference numerals denote like elements throughout the drawings.

Figure 2:
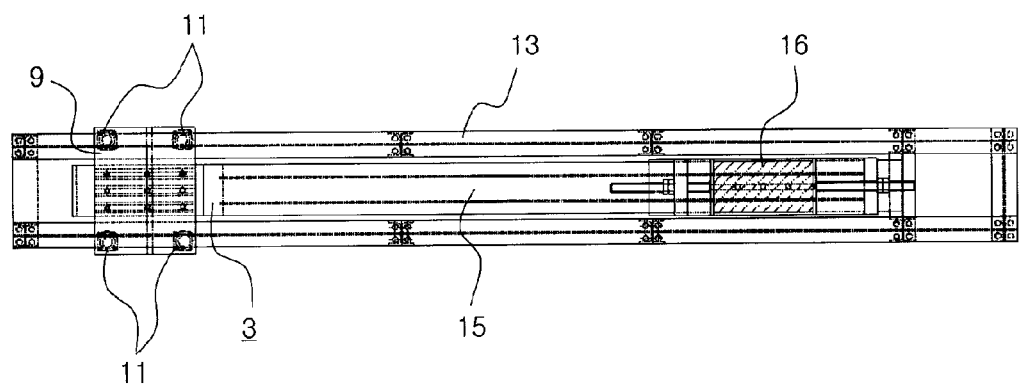
FIG. 2 is a plan view of the creep tester illustrated in FIG. 1.
Figure 3:
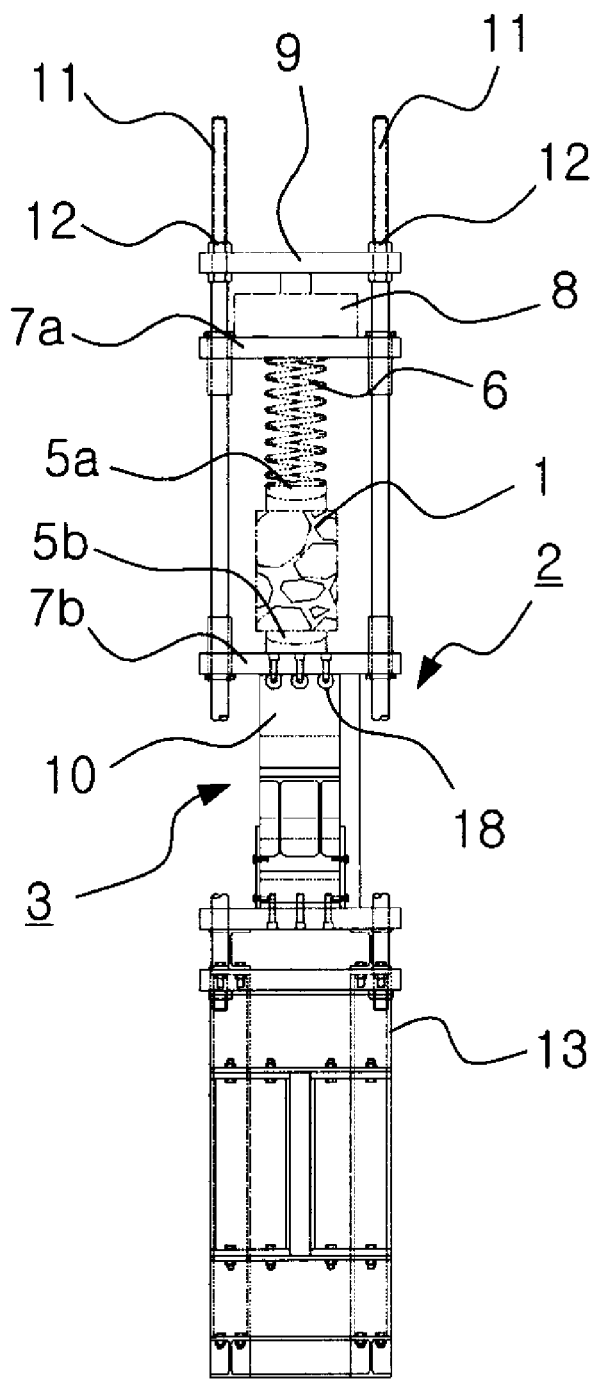
FIG. 3 is a side view taken in the direction of arrow A illustrated in FIG. 1.
Figure 4:
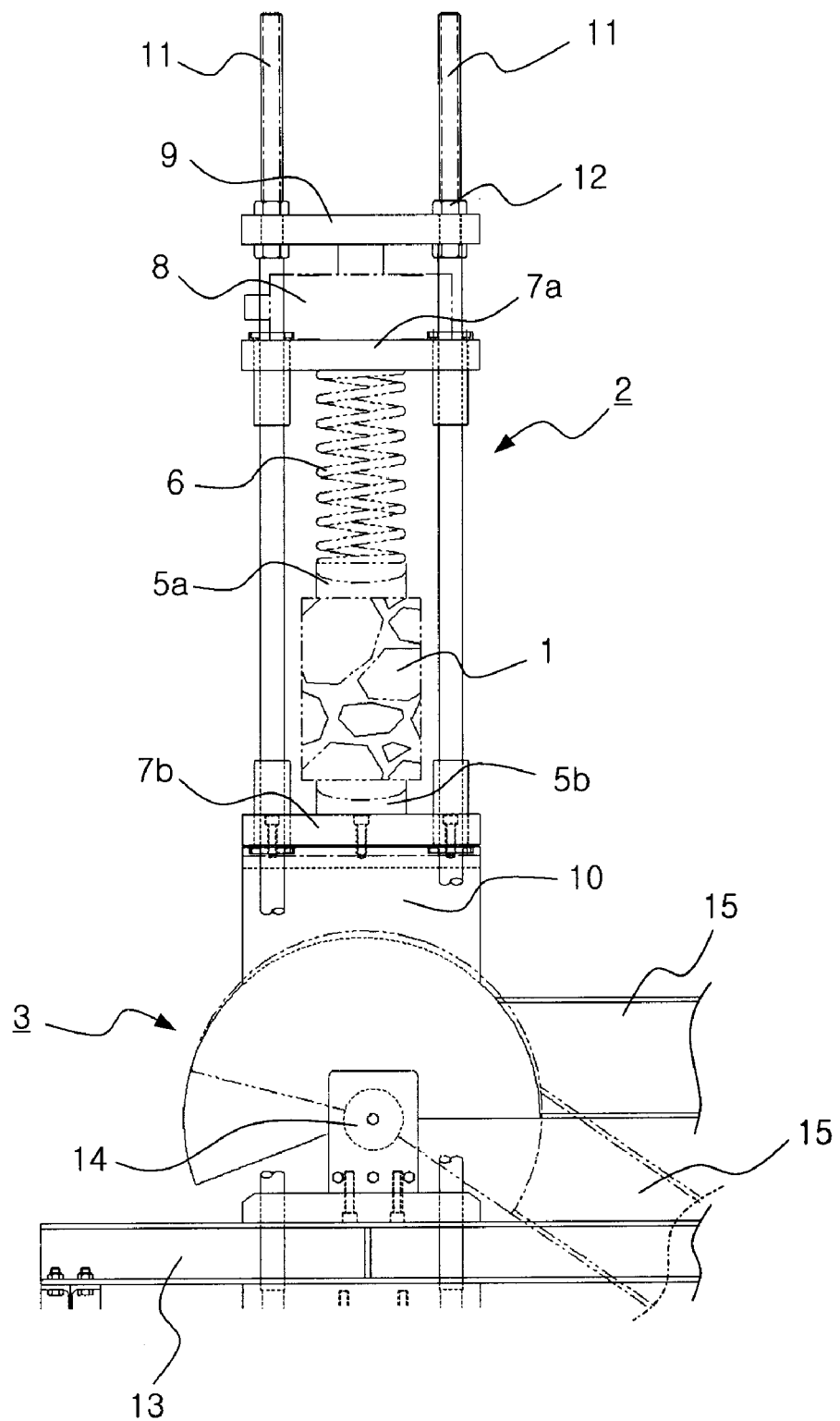
FIG. 4 is a partially enlarged view of the creep tester illustrated in FIG. 1.
Figure 5:
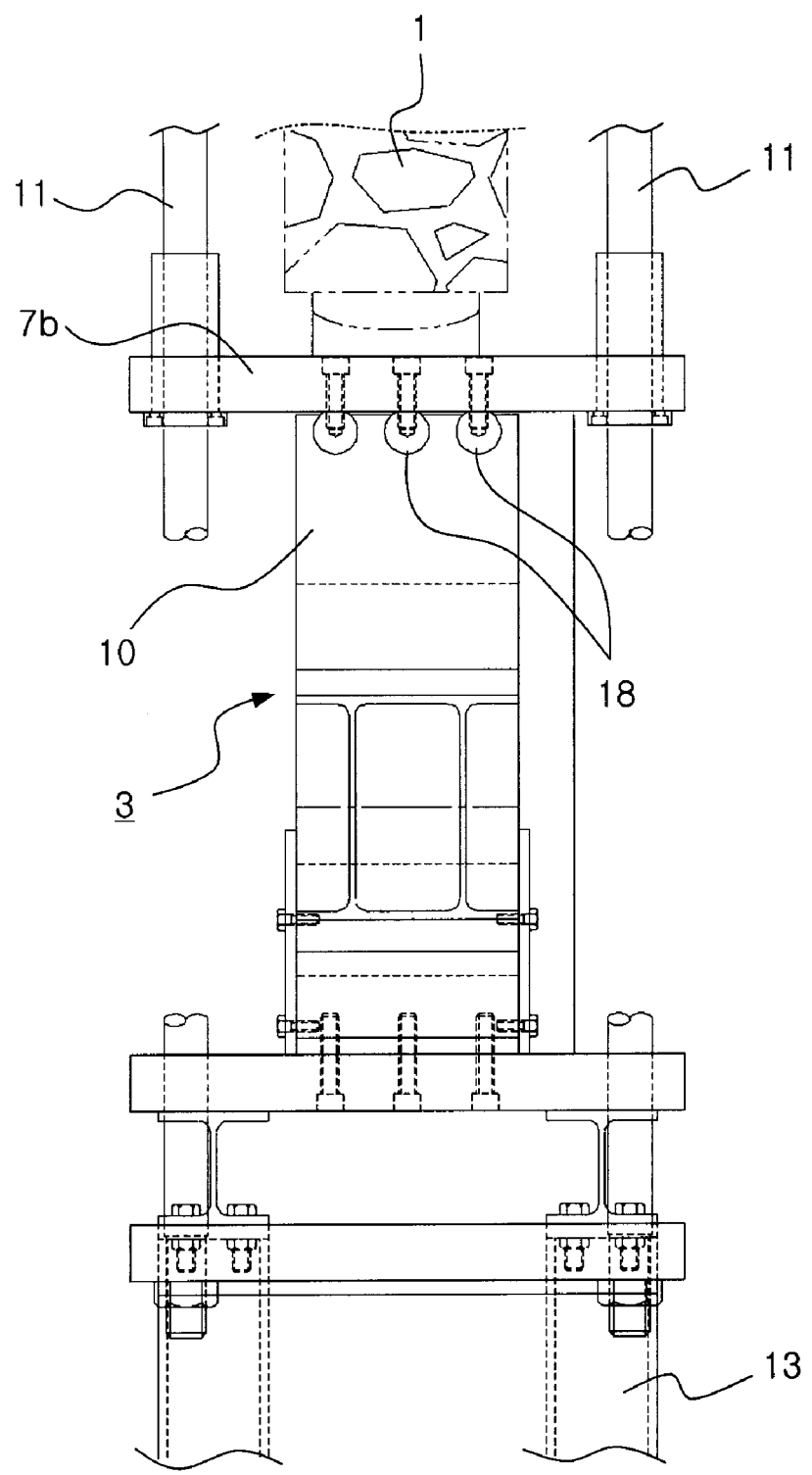
FIG. 5 is a partially enlarged view of the creep tester illustrated in FIG. 3.

FIG. 1 is a front view of a creep tester for precise load control with a self load according to an exemplary embodiment of the present invention, FIG. 2 is a plan view of the creep tester illustrated in FIG. 1, FIG. 3 is a side view taken in the direction of arrow A in FIG. 1, and FIGS. 4 and 5 are partially enlarged views of FIGS. 1 and 3.

Referring to FIG. 1, the creep tester according to this example embodiment is configured to measure creep characteristics of construction material such as a concrete specimen 1. The creep tester includes a movable actuator 2 capable of loading corresponding to change in length of the concrete specimen 1, a cam actuator 3 operated in association with the movable actuator 2, and a self weight actuator 4.

The movable actuator 2 includes upper and lower spherical adjusting seats 5a and 5b to hold upper and lower portions of the concrete specimen 1, a spring 6 disposed on the upper spherical adjusting seat 5a to react corresponding to a minute deformation of the concrete specimen 1, upper and lower movable tables 7a and 7b respectively contacting the spring 6 and the lower spherical adjusting seat 5b, a load cell 8 and a stationary table 9 disposed on the upper movable table 7a, and a movable loading table 10 disposed under the lower movable table 7b to apply a predetermined load to the concrete specimen 1. The upper and lower movable tables 7a and 7b are stationary in the horizontal direction and can be moved along four tensile load columns 11 in the vertical direction.

The load cell 8 is disposed on the upper movable table 7a to measure an applied load, and is provided at an upper side with the stationary table 9, which is secured to the tensile load columns 11 by nuts 12 to hold the load cell 8.

The cam actuator 3 is located under the movable loading table 10 of the movable actuator 2, and is configured to actuate based on the principle of cam operation. The cam actuator 3 is configured to operate based on a principle of cam operation, and includes a cam having a semi-cylindrical column, and a securing shaft 14 fixed to a supporting frame 13 biased to one side from a center of the cam secured to the securing shaft 14, such that the cam of the cam actuator 3 can be rotated about the securing shaft 14. When the cam of the cam actuator 3 is rotated about the securing shaft 14, a distance between an upper surface of the movable loading table 10 of the movable actuator 3 and the securing shaft 14 of the cam actuator 3 is increased or decreased.

Based on the principle of cam operation, the creep tester applies a compressive force to the concrete specimen 1.

Further, the self-weight actuator 4 for actuating the cam actuator 3 includes a moment beam 15 disposed at one side of the self-weight actuator 4, a mass 16 located at one end of the moment beam 15 to supply an applied load, and a mass adjuster 17 connected to the mass 16 to adjust the applied load. With the self-weight actuator 4, the applied load can be adjusted to adjust the length of the moment beam 15.

For example, when moving the mass 16 on the moment beam 16 with the mass adjustor 17 in a forward or rearward direction to change the location of the mass 16 on the moment beam 15, the applied load can be adjusted according to the principle of leverage.

Next, operation and advantageous effects of the creep tester are described.

In operation of the cam actuator 3 and movable actuator 2, the lower movable table 7b is secured to the tensile load columns 11 in the horizontal direction, and three cylindrical guides 18 secured to the lower movable table 7b are fitted into the movable loading table 10. The movable loading table 10 of the movable actuator 2 has a semi-circular lower surface machined corresponding to the shape of the cam actuator 3. When the cam actuator 3 is rotated, the movable loading table 10 moves minutely in the horizontal direction towards the moment beam 15 while moving along the tensile load columns 11 in the vertical direction.

The operational principle of the creep tester is based on the principle of the cam and leverage operation such that the weight of mass 16 is applied to a concrete specimen 1 during testing.

When a load is applied in a vertically downward direction by the weight of mass 16 loaded on the end of the moment beam 15, the concrete specimen 1 prepared for creep test is lowered to a location indicated by a dotted line, as illustrated in FIG. 1, where the creep tester is in an actuation state. Then, the cam actuator 3 connected to the moment beam 15 is rotated forcibly about the securing shaft 14 by the principle of leverage, causing the movable loading table 10 of the movable actuator 2 to be minutely raised according to the principle of cam operation (see, e.g., FIG. 4). Further, the lower movable table 7b coupled to the movable loading table 10 via the cylindrical guides 18 is raised.

As a result, the movable loading table 10, and upper and lower movable table 7a and 7b slide along the tensile load columns 11 that are fitted into holes formed at respective corners of the movable loading table 10, and upper and lower movable table 7a and 7b.

Then, the load is measured by the load cell 8 disposed on the upper movable table 7a. At this time, if the applied load is not suitable, the load is adjusted by adjusting the mass 16 on the moment beam 15 using the mass adjuster 17. The stationary table 9 disposed above the load cell 18 is a rectangular plate to support reaction force with respect to the load applied by the cam actuator 3, and has holes respectively formed at four corners such that the stationary table 9 is secured by the tensile load columns 11 fitted into the holes while being secured by the securing nuts 12 in the vertical direction.

Although the creep tester is applied to the creep test for the concrete specimen 1 in the above description, it should be appreciated that the creep tester can also be applied to measurement of mechanical properties of material, such as compressive strength, etc.

As apparent from the above description, the creep tester is configured to measure creep characteristics of concrete and other general materials. With the creep tester, a compressive force is applied to a specimen from a lower side of the specimen according to a cam and leverage principle, with upper and lower portions of the specimen secured by a movable table and tensile load columns. To solve the problems of the conventional creep tester caused by non-continuity of hydraulic pressure and use of a separate electrical device and manual operation, the creep tester is provided with a mass at one end of a lever to move downwardly in association with slide of the cam and movable table so as to apply a constant force to the specimen when the length of specimen decreases due to a creep phenomenon, so the specimen undergoes a constant compressive force irrespective of the decrease in length of the specimen caused by the creep phenomenon.

Further, the creep tester can measure a decreasing length of the specimen while applying a load to the specimen. According to a conventional method of measuring the decreasing length, a dial gauge, etc., are used to measure a variable length between marks preset on upper and lower portions of the specimen. The creep tester can measure the amount of creep based on a downward movement of the distal end of the lever, which geometrically corresponds to the decreasing length of specimen in the creep tester. Therefore, the creep tester can measure a more precise amount of creep and provides a more convenient creep test.

Although the present invention has been described with reference to example embodiments and the accompanying drawings, the present invention is not limited to these example embodiments or the drawings. Further, it should be understood that various modifications and changes can be made by those skilled in the art without departing from the spirit and scope of the present invention.

What is claimed is:

1. A creep tester for measuring a creep characteristic of a construction material, comprising:

a movable actuator for applying a constant load to a specimen made from the construction material corresponding to changes in length of the specimen;

a cam actuator operatively coupled with the movable actuator for applying the load to the latter, wherein the cam actuator includes a cam rotatably mounted on a securing shaft, and has a substantially semi-cylindrical column; and a self-weight actuator fixedly coupled with the cam actuator for delivering the load to actuate the cam actuator, wherein the movable actuator includes upper and lower spherical adjustment seats configured to hold upper and lower portions of the specimen, a spring disposed on the upper spherical adjustment seat configured to react corresponding to a minute deformation of the specimen, upper and lower movable tables respectively contacting the spring and the lower spherical adjustment seat, and configured to be moved along four tensile load columns in a vertical direction while being secured to the four tensile load columns in a horizontal direction, a load cell and a stationary table disposed on the upper movable table, and a movable loading table disposed under the lower movable table configured to apply a predetermined load to the specimen.

2. The creep tester according to claim 1, wherein the stationary table is disposed on the load cell and is secured to the tensile load columns by nuts to hold the load cell.

3. The creep tester according to claim 1, wherein the cam actuator is located under the movable loading table to operate the movable actuator according to a principle of cam operation, wherein the movable loading table is coupled to the lower movable table of the movable actuator through cylindrical guides, and wherein the securing shaft of the cam actuator is fixed to a supporting frame biased from a center of the cam.

4. The creep tester according to claim 1, wherein the self weight actuator includes a moment beam disposed at one side of the self weight actuator, a mass located at one end of the moment beam to supply an applied load, and a mass adjuster connected to the mass to adjust the applied load.

* * * * *